United States Patent
Fini et al.

[11] Patent Number: 5,837,140
[45] Date of Patent: Nov. 17, 1998

[54] BLOOD FILTER AND EXTRACORPOREAL CIRCUIT

[75] Inventors: Massimo Fini, Mirandola; Nicola Ghelli, Casale; Giuseppe Grandi, Felice, all of Italy

[73] Assignee: Dideco S.p.A, Mirandola, Italy

[21] Appl. No.: 652,671

[22] Filed: May 28, 1996

[30] Foreign Application Priority Data

May 29, 1995 [IT] Italy .................................. MI95A1114
May 29, 1995 [IT] Italy .................................. MI95A1115

[51] Int. Cl.$^6$ ............................. B01D 29/05; B01D 29/07
[52] U.S. Cl. .......................... 210/483; 210/295; 210/435; 210/436; 210/493.1; 210/493.5; 210/499
[58] Field of Search ..................................... 210/252, 295, 210/435, 436, 454, 483, 488, 489, 483.1, 446, 493.5, 499; 604/4

[56] References Cited

U.S. PATENT DOCUMENTS

| | | | |
|---|---|---|---|
| 3,593,854 | 7/1971 | Swank | 210/446 |
| 3,765,536 | 10/1973 | Rosenberg | 210/446 |
| 3,935,111 | 1/1976 | Bentley | 210/446 |
| 4,056,476 | 11/1977 | Mouwen et al. | 210/446 |
| 4,252,653 | 2/1981 | Beck et al. | 210/446 |
| 4,479,874 | 10/1984 | Rosenberg et al. | 210/446 |
| 5,540,841 | 7/1996 | Gsell et al. | 210/446 |
| 5,599,448 | 2/1997 | Spearman | 210/446 |
| 5,618,425 | 4/1997 | Mitamura et al. | 210/446 |

*Primary Examiner*—John Kim
*Attorney, Agent, or Firm*—Popovich & Wiles, P.A.

[57] ABSTRACT

The present invention provides a blood filter comprising a housing having a top portion, a base portion and a sidewall portion and a blood inlet. A filter element is disposed within the housing and divides the housing into an inlet chamber in flow communication with the blood inlet and an outlet chamber. The filter element comprises a portion of non-woven filter material and a portion of screen filter material and both the non-woven filter material portion and the screen filter material portion are in contact with the inlet chamber and the outlet chamber. The housing also comprises a blood outlet in flow communication with the outlet chamber.

19 Claims, 7 Drawing Sheets

BLOOD FILTER AND EXTRACORPOREAL CIRCUIT

FIELD OF THE INVENTION

This invention relates to blood reservoirs and blood filters. More particularly, this invention relates to a cardiotomy reservoir for collecting blood and to a blood filter for use in extracorporeal blood circuits commonly used during various surgical procedures, such as open-heart surgery.

BACKGROUND OF THE INVENTION

Many surgical procedures require that a patient's blood be diverted outside the body. For example, during open heart surgery a patient's blood must be directed around the heart and lungs in an extracorporeal circuit. Extracorporeal circuits generally include devices for performing various processes on the blood, e.g., oxygenation, filtration, heating, and storage. Other procedures requiring the routing of blood through an extracorporeal circuit include autotransfusion and extracorporeal membrane oxygenation for long term support.

Extracorporeal circuits are typically set up by an individual known as a perfusionist. The perfusionist controls the rate of blood flow and other blood parameters and operates the various devices connected in the circuit. Extracorporeal circuits generally include oxygenators, heat exchangers, and filters, which are either interconnected by surgical tubing or an integrated structure. In a typical cardiopulmonary bypass surgical procedure, a bypass circuit is created in which venous blood bypasses the heart and is reintroduced into an artery after being oxygenated. Also, cardiotomy blood is scavenged from the surgical site, combined with the venous blood, oxygenated, and reintroduced into the patient. The extracorporeal bypass circuit performs numerous functions, including removing emboli and particulate matter from the blood, regulating the carbon dioxide and oxygen content of the blood, and regulating the blood temperature.

Extracorporeal circuits also include blood reservoirs. A blood reservoir is an enclosure in which blood is temporarily stored. The storage of blood in reservoirs assists in regulation of the patient's blood volume and pressure. Cardiotomy reservoirs are used for collecting blood from the surgical site and usually include a container that is placed under negative pressure to aspirate the blood from the surgical site. Because this blood comes from the surgical site, it contains clots and various impurities.

A common form of cardiotomy reservoir has a filter on the blood inlet. After the blood passes through the filter, it passes into the main portion of the reservoir. The blood in the reservoir is clean enough to be reinfused into the patient. On the lid of the cardiotomy reservoir there is an outlet connector which is connected to a tube that draws from a trap provided at the bottom of the reservoir.

This type of cardiotomy reservoir is useful if a lot of blood is lost during the operation. However, operating techniques are evolving towards reducing the amount of blood loss during surgery, and therefore it is often desirable to collect the small amounts of blood that are found only in order to evacuate them. Accordingly, a very simple cardiotomy reservoir without a filter may be used.

However, if blood that has been collected in a cardiotomy reservoir having no filter is to be recovered, this recovery may be performed by combining the cardiotomy reservoir with an external filter only if it is possible to aspirate the blood from the trap located on the bottom of the reservoir. This blood may contain clots or impurities that may prevent or impede aspiration.

The cardiotomy reservoir of the present invention improves upon the prior art by providing a cardiotomy reservoir in which there is a filter between the trap and the main portion of the reservoir so that blood may be aspirated out of the trap without clogging. The reservoir is made of simple materials and is easy to use.

Many types of blood filters have been used in extracorporeal circuits. Two filtering materials used in the art are a screen filter and a non-woven filter. A screen filter provides surface filtration with excellent fluid-dynamics characteristics because it allows blood flow with minimal resistance. A non-woven filter provides a depth filter with high resistance to the passage of the blood. Screen filters are more difficult to manufacture than non-woven filters. Accordingly, screen filters are usually more expensive than non-woven filters.

In some filters, use of a non-woven filter, induced by the need to provide a low cost product, causes air bubbles to remain trapped within the blood mass. The presence of air bubbles prevents correct operation of the line that contains the filter because of continuous stoppages caused by the safety systems that detect the presence of air bubbles.

The blood filter of the present invention improves upon the prior art by providing a hybrid blood filter that has a filter element with both a screen filter portion and a non-woven filter portion. This blood filter provides the advantages of a screen filter with the low cost and ease of manufacture of a non-woven filter.

SUMMARY OF THE INVENTION

The present invention provides a cardiotomy reservoir for containing blood comprising a housing having a top portion, a bottom portion, and a continuous sidewall portion, the top portion and bottom portion connected to the sidewall portion to form an enclosed reservoir. The housing has a blood inlet, a blood outlet, and an air outlet. The housing also has a trap at the bottom portion of the housing and the blood outlet is connected to a tube that draws from the trap at the bottom portion of the housing. The housing has a filter interposed between the trap and the inside of the main portion of the housing. This cardiotomy reservoir may be used in an extracorporeal circuit.

The present invention also provides a blood filter comprising a housing having a top portion, a base portion and a sidewall portion and a blood inlet. A filter element is disposed within the housing and divides the housing into an inlet chamber in flow communication with the blood inlet and an outlet chamber. The filter element comprises a portion of non-woven filter material and a portion of screen filter material and both the non-woven filter material portion and the screen filter material portion are in contact with the inlet chamber and the outlet chamber. The housing also comprises a blood outlet in flow communication with the outlet chamber. This blood filter may be used in an extracorporeal circuit. Both the cardiotomy reservoir and the blood filter may be used in the same extracorporeal circuit.

Additional features and advantages of the invention are set forth in the description which follows and in part will be apparent from the description. The objectives and other advantages of the invention will be realized and attained by the cardiotomy reservoir and blood filter and their uses as particularly pointed out in the written description, claims, and appended drawings.

It is to be understood that both the foregoing general description and the following detailed description are exemplary and explanatory and are intended to provide further explanation of the invention as claimed.

BRIEF DESCRIPTION OF THE DRAWINGS

For a better understanding of the invention, the appended drawings illustrate embodiments of the invention and with the description serve to explain the principles of the invention.

DETAILED DESCRIPTION OF THE INVENTION

The invention provides a cardiotomy reservoir and a blood filter. Both the reservoir and filter may be used in extracorporeal blood circuits.

The cardiotomy reservoir comprises a housing having a top portion, a bottom portion, and a continuous sidewall portion. The top portion and bottom portion are connected to the sidewall portion to form an enclosed reservoir. The housing has a blood inlet, a blood outlet, and an air outlet. The housing also has a trap at the bottom portion of the housing. The blood outlet is connected to a tube that draws from the trap at the bottom portion of the housing, and the housing has a filter interposed between the trap and the inside of the main portion of the housing. In a preferred embodiment the filter is a foam filter with a pore size of 5 to 50 pores per inch (ppi), more preferably 20 to 30 ppi. The filter may be a polyurethane foam filter. In another preferred embodiment, the filter is dome-shaped and contacts a substantial portion of the inside bottom portion of the housing.

The housing may be semirigid. "Semirigid" means that the housing has a rigidity in between that of a typical hardshell reservoir that has a high rigidity and a typical soft bag reservoir that has negligible rigidity. An example of a material that is semirigid is the plastic used for consumer beverage bottles. The housing is made of a blood compatible material, usually plastic. The housing is preferably clear so the level of blood within the reservoir may be seen.

The invention also provides a cardiotomy reservoir further comprising a rigid support structure for the cardiotomy reservoir. A support structure is especially useful if the reservoir is semirigid. When a semirigid reservoir is subjected to a vacuum, it will tend to implode somewhat. The rigid support structure supports the semirigid reservoir so the walls will not implode under the vacuum used for blood aspiration. In a preferred embodiment the rigid support structure encloses the cardiotomy reservoir. In use, only the enclosed reservoir is subjected to a vacuum. The rigid support structure preferably is cylindrical and only slightly larger in diameter than the cardiotomy reservoir.

The reservoir may be disposable. In a preferred embodiment, the reservoir is disposable and semirigid. The disposable, semirigid reservoir is preferably used in a non-disposable, cylindrical rigid support structure.

In a preferred embodiment, one or more of the blood inlet, blood outlet, and air outlet are located on the top portion of the housing. The air outlet preferably is adapted for connection to a vacuum source. In use, the air inlet is connected to a vacuum source to operate the reservoir. In a preferred embodiment, the trap has a bottom portion adapted to be convertible to a blood outlet.

Figure 5:
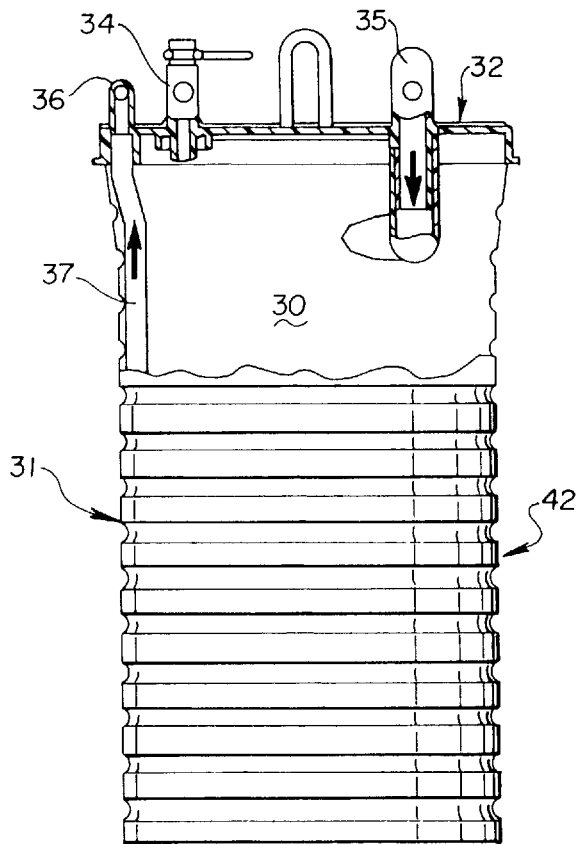
FIG. 5 is a side perspective view of a cardiotomy reservoir of the present invention.

FIG. 5 shows a cardiotomy reservoir 30 of the present invention. Reservoir 30 has a housing 42 having a top 32, a continuous sidewall 31, and a bottom portion 41. At the bottom portion 41 of the housing 42 is a trap 33.

Figure 6:
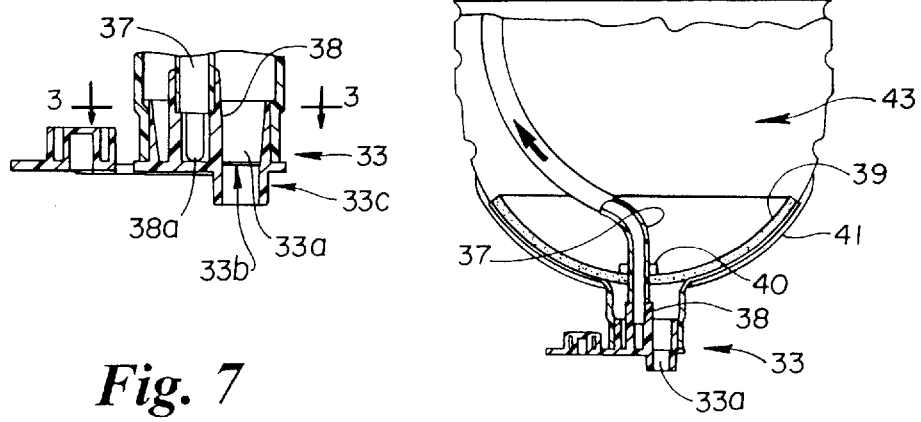
FIG. 6 is a side cross-sectional view of a trap of a cardiotomy reservoir of the present invention.
Figure 7:
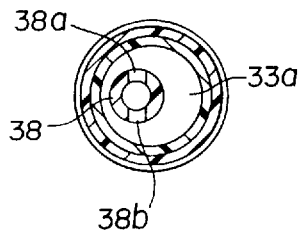
FIG. 7 is a top cross-sectional view of a trap of a cardiotomy reservoir of the present invention.

The air outlet 34 on the top 32 may be connected to a vacuum line to place the container under negative pressure and aspirate blood from a surgical field through one or more lines that reach the blood inlet 35, which leads directly into the container. The blood outlet 36 on the top 32 is connected to the tube 37 that draws from inside the trap 33. Referring to FIGS. 5 to 7, the end of the tube 37 is inserted in the connector 38. Connector 38 extends from the bottom of the trap 33 and has ports 38a and 38b, which allow the passage of the blood from the space 33a into the tube 37.

A main feature of the cardiotomy reservoir 30 is the presence of a filter 39 interposed between the space 33a that lies within the trap and the main portion 43 of the housing 42. The filter 39 prevents access to space 33a by clots and impurities, which might possibly clog the inlet section of the tube 37 and prevent aspiration through the tube 37.

In the illustrated embodiment, the filter 39 is shaped like a dome, makes contact with a large portion of the bottom portion 41 of the housing 42 inside which the trap 33 is formed, and is provided with a hole for the passage of the tube 37, complete with a gasket 40. The filter may have any shape, provided that it is adapted to be interposed in the passage of the blood from the main portion of the housing to the trap 33. It is preferred that the filter make contact with a large portion of the bottom portion of the housing inside which the trap is formed so that there is good adherence between the filter and the trap and so there is sufficient filtering surface if a large number of clots are present. Blood may flow either directly through the filter 39, from the main portion 43 of the housing 42 to the trap 33, or flow from the main portion 43 of the housing 42, into the filter 39, flow laterally through the filter 39, and then into the trap 33.

Trap 33 also has bottom portion 33b and blood outlet 33c. In addition to aspirating the blood out through tube 37 and blood outlet 36, blood may also flow out blood outlet 33c. Bottom portion 33b of the trap 33 must be punctured or removed to allow blood to flow through blood outlet 33c.

Accordingly, the blood contained in the trap 33 is free of clots of blood or impurities that might clog the inlet section of the tube 37 and prevent or impede blood aspiration through the tube 37 if the blood is to be retrieved through tube 37.

The invention provides a blood filter comprising a housing having a top portion, a base portion and a sidewall portion and a blood inlet. A filter element is disposed within the housing and divides the housing into an inlet chamber in flow communication with the blood inlet and an outlet chamber. The filter element comprises a portion of non-woven filter material and a portion of screen filter material and both the non-woven filter material portion and the screen filter material portion are in contact with the inlet chamber and the outlet chamber. The housing also comprises a blood outlet in flow communication with the outlet chamber. In a preferred embodiment, the screen filter material portion contacts less of the inlet chamber than the non-woven filter material portion.

In a preferred embodiment, the blood inlet is located at the base portion of the housing and the blood outlet is located at the top portion of the housing. In a preferred embodiment, the top portion of the housing has inclined surfaces converging upwardly towards the blood outlet. In another embodiment, the housing is generally rectangular. The housing is made of a blood compatible material, usually plastic. The housing is preferably clear so the level of blood within the filter may be seen.

The filter element is preferably in the form of a continuous folded sheet. However, the filter element may be any shape. Preferably, the filter element is supported by a support and the filter element has upper and lower ends which are embedded in potting. The support for the filter element preferably comprises a plurality of substantially parallel flaps that are H-shaped and are connected at a central region, so as to form a plurality of regions for blood passage. Preferably, the filter element comprises folds, each one of the folds of the portion of the filter element constituted by the non-woven filter material is supported by a half-flap of the support and the folds of the screen filter material portion of the filter element are disposed within two adjacent half-flaps of the support. In a preferred embodiment, the inlet chamber is surrounded by the outlet chamber.

Preferably, the non-woven filter material has a nominal porosity of from 10 to 100 microns, more preferably of from 20 to 50 microns. The non-woven filter material is preferably a polyester felt. Preferably, the screen filter material has an aperture size of from 10 to 100 microns, more preferably of from 20 to 50 microns. The screen filter material is preferably a polyester screen.

The invention also provides an extracorporeal circuit comprising one or both of the cardiotomy reservoir and blood filter of the invention. In a preferred embodiment, the extracorporeal circuit comprises both the cardiotomy reservoir and blood filter of the invention.

Figure 1:
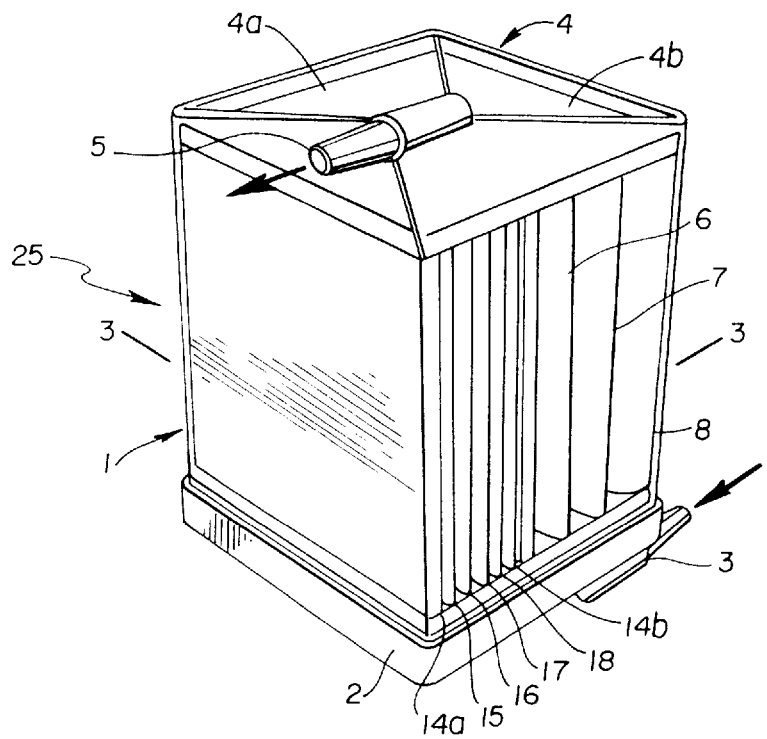
FIG. 1 is a perspective view of a blood filter of the present invention.
Figure 2:
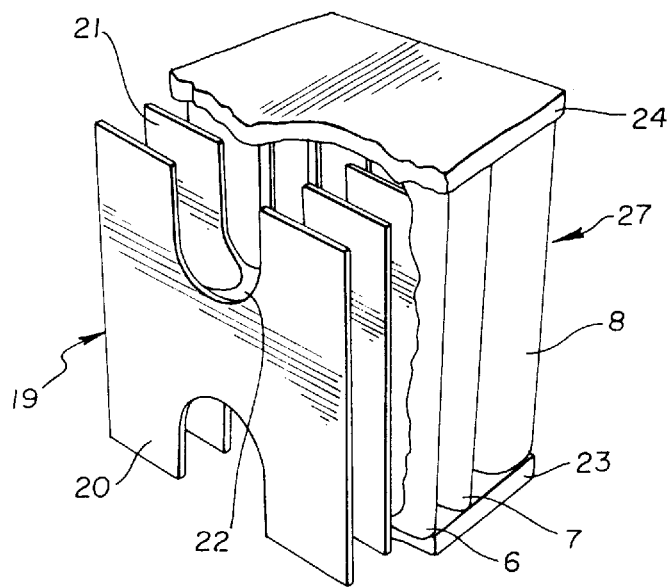
FIG. 2 is a perspective view of a blood filter of the present invention.

FIG. 1 shows a blood filter 25 of the present invention. Blood filter 25 has a housing 1 having a top portion 4, a base portion 2, and a sidewall portion 26. The base portion 2 has a blood inlet 3 for the blood to be filtered. The top portion 4 has a blood outlet 5. Top portion 4 has surfaces 4a and 4b which are tilted upward and converge towards the blood outlet 5.

The filter element 27 is provided in the form of a continuous folded sheet in which the portion of the filter element 27 folded in 6, 7, 8, 9, 10, 11, 12, and 13 is formed by non-woven filter material; the portion of the filter element folded in 15, 16, 17, and 18 is made of screen filter material and is welded to the non-woven filter material portion on the sides 14a and 14b.

The continuous folded sheet of filter element 27 is supported by a support 19, formed by a plurality of substantially parallel flaps such as 20 and 21 that are H-shaped and are connected at the central region, as in 22 for the flaps 20 and 21, so as to provide wide regions for blood passage.

An inlet chamber 28 is thus formed which is delimited laterally by the continuous folded sheet of filter element 27, in its two portions made of non-woven filter material and screen filter material, and at the upper and lower ends of the filter element 27 by layers of polyurethane resin 23 and 24, known as potting, in which the folded sheet of filter element 27 and the support 19 are embedded. Other types of potting may also be used. The blood to be filtered is introduced into the inlet chamber 28 by the blood inlet 3.

Figure 3:
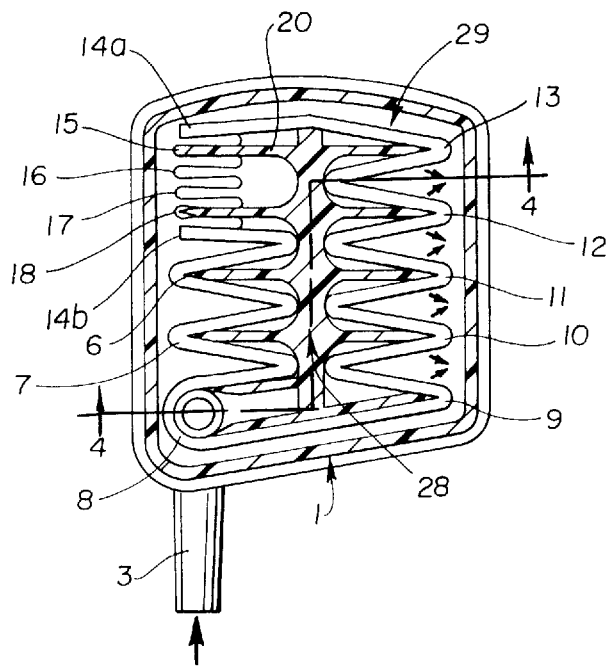
FIG. 3 is a cross-sectional view taken along the plane III—III of FIGS. 1 and 4 of a blood filter of the present invention.
Figure 4:
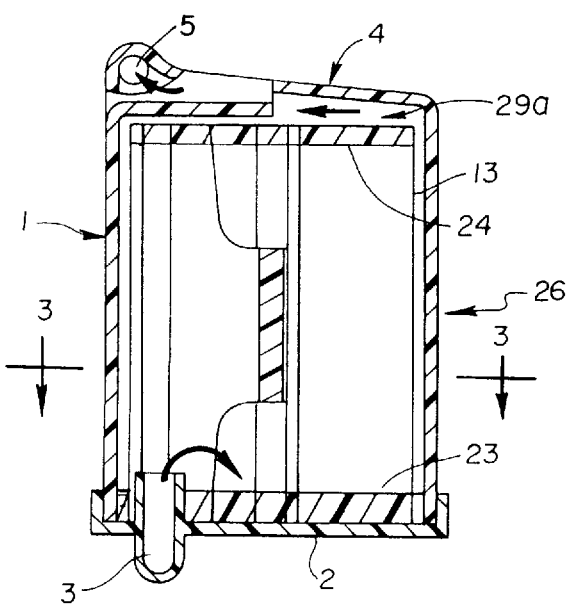
FIG. 4 is a cross-sectional view taken along the plane IV—IV of FIG. 3 of a blood filter of the present invention.

Blood inlet 3 is inserted between two flaps of the support 19 and the blood to be filtered is sent into the inlet chamber 28 of the filter 25. The filter 25 fills uniformly because of the wide passage spaces provided by the H-like shape of the flaps such as 20 and 21. The inlet chamber 28 is delimited by the continuous folded sheet of filter element 27. The blood then flows out, filtered, according to the arrows shown in FIG. 3, into the outlet chamber 29, which is delimited by the housing 1, to flow towards the blood outlet 5. The blood filter 25 involves in an active flow the entire mass of blood contained in the upper chamber 29a of the filter 25 by virtue of the presence of the inclined surfaces 4a and 4b of the top portion 4.

The primary function performed by the screen filter portion, despite being much smaller than the non-woven filter portion, is easily understood. As mentioned earlier, non-woven filter material provides intense resistance to the blood flow. If the sheet of filter element was entirely formed of non-woven filter, when the operation begins with the filter full of air, the level of the blood rising gradually from the base 2 would be considerably higher inside the inlet chamber 28 than inside the outlet chamber 29. Therefore air bubbles would remain trapped in the outlet chamber 29 and the air bubbles would then be mixed in with the output filtered blood. The presence of air bubbles in the filtered blood would cause frequent interruptions of operation, caused by the safety systems. The presence of the screen filter material portion allows the level of the rising blood to be the same in both the inlet chamber 28 and outlet chamber 29, and thus bubble elimination is easy and immediate.

Figure 8:
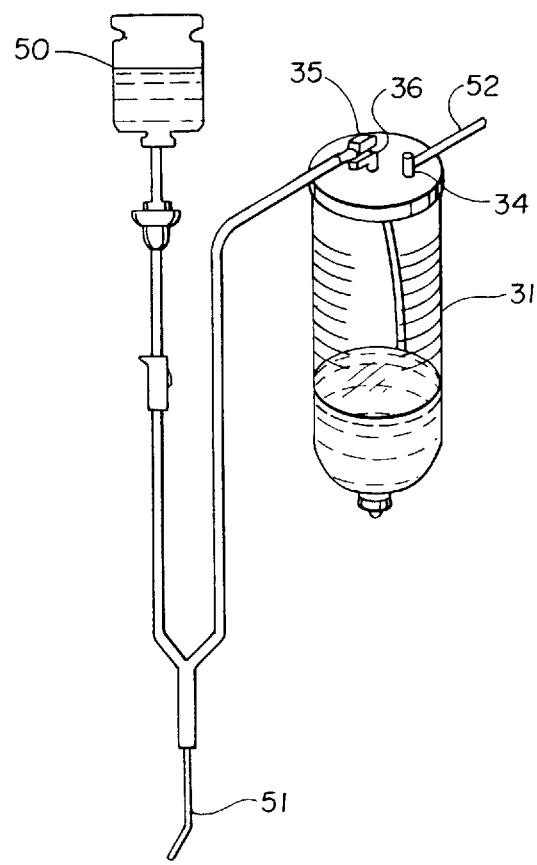
FIG. 8 is a schematic of an apparatus for collecting blood using a cardiotomy reservoir of the present invention.

FIG. 8 shows the use of the cardiotomy reservoir 31 to aspirate blood from the operating field. Suction cannula 51 aspirates blood which flows to blood inlet 35. Line 52, attached to air outlet 34, goes to a vacuum source. Anticoagulant solution bag 50 adds anticoagulant to the aspirated blood.

Figure 9:
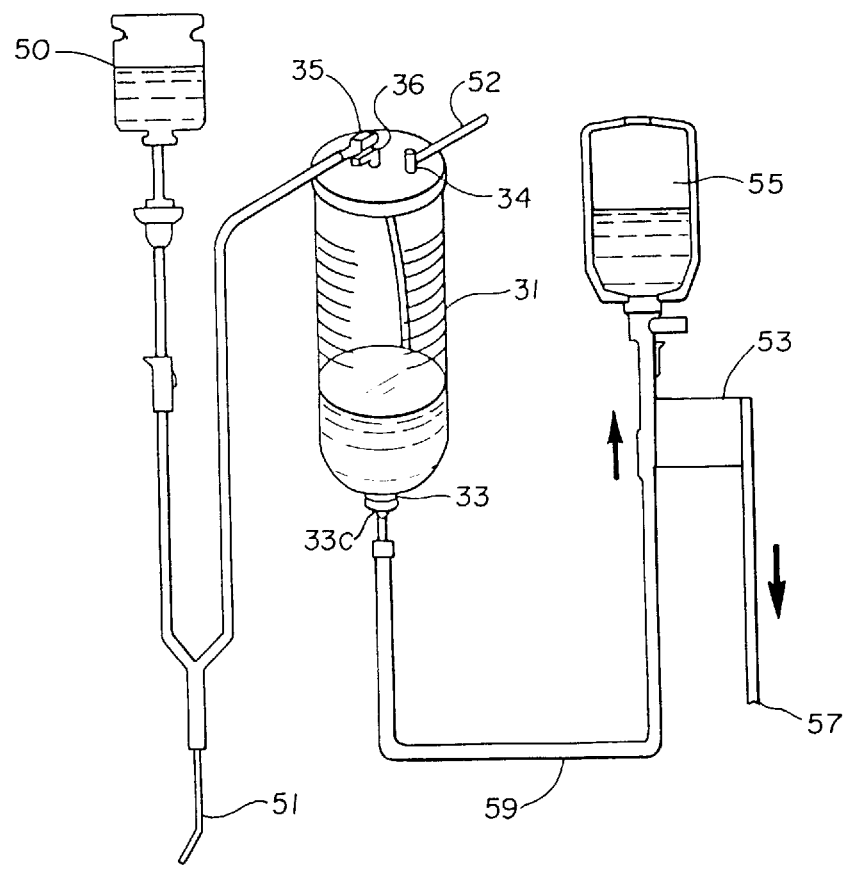
FIG. 9 is a schematic of an apparatus for collecting and filtering blood using a cardiotomy reservoir and a blood filter of the present invention.

FIG. 9 shows the use of the cardiotomy reservoir 31 and the blood filter 53. Blood flows from trap 33 through blood outlet 33c. As noted above, to use blood outlet 33c, bottom portion 33b of the trap must be punctured or removed. Blood flows from blood outlet 33c through line 59 into drainage bag 55 and then into blood filter 53. The filtered blood is returned to the patient through line 57. This arrangement is used when no blood washing is needed.

Figure 10:
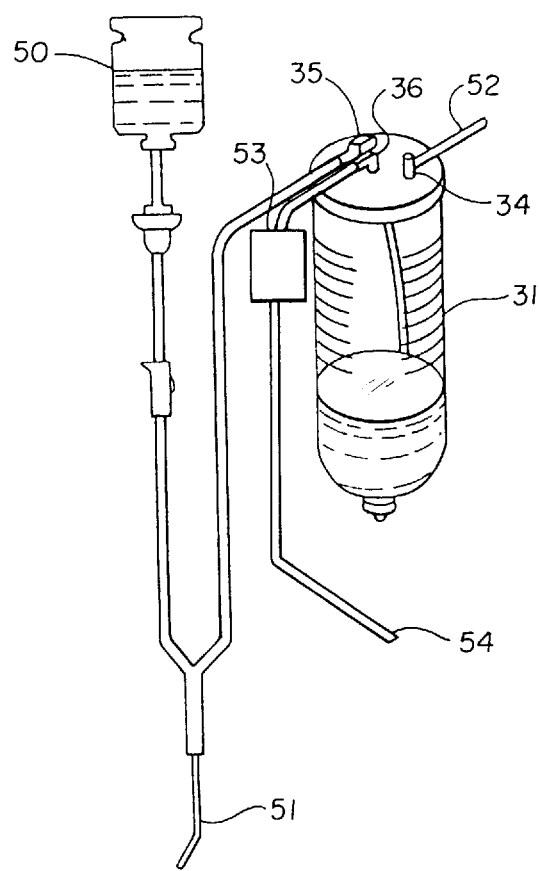
FIG. 10 is a schematic of an apparatus for collecting and filtering blood using a cardiotomy reservoir and a blood filter of the present invention.

FIG. 10 shows another use of the cardiotomy reservoir 31 and the blood filter 53. Blood exits through the blood outlet 36 and goes to blood filter 53. The blood then flows through line 54 to an autotransfusion machine.

Figure 11:
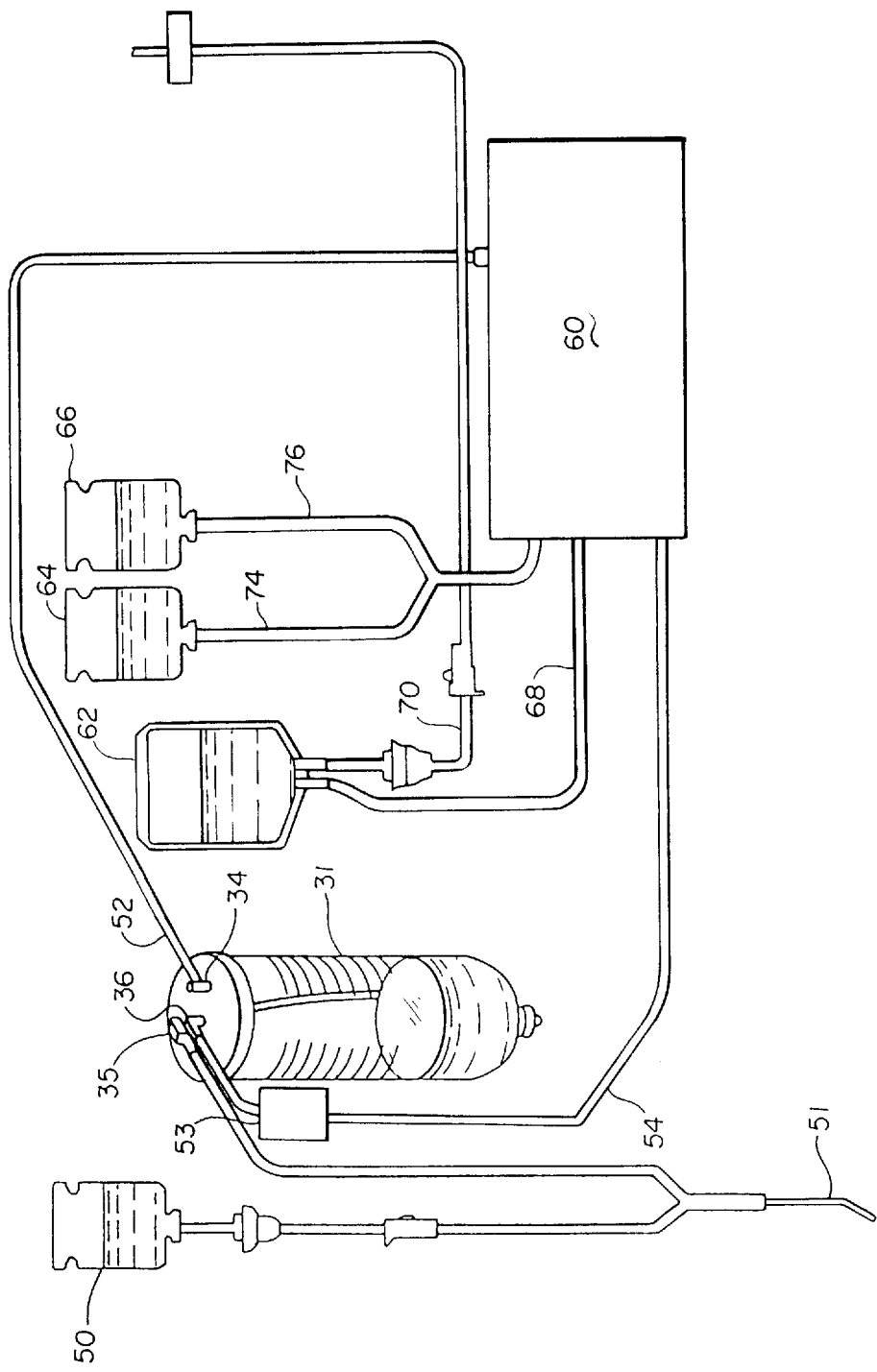
FIG. 11 is a schematic of an apparatus for collecting and filtering blood using a cardiotomy reservoir and a blood filter of the present invention.

FIG. 11 shows more detail of a possible arrangement using an autotransfusion machine. Blood flows through line 54 to autotransfusion machine 60. Washing solution flows from washing solution bags 64 and 66 through lines 74 and 76 into the autotransfusion machine 60. Washed blood flows through line 68 into reinfusion bag 62 and blood flows out through line 70 back to the patient. Line 52 provides a vacuum to the cardiotomy reservoir 31.

In the practical embodiment of the invention, all the details may be replaced with other technically equivalent elements; the shapes and the dimensions, as well as the materials employed, may also be any according to the requirements.

The above description and accompanying drawings are provided for the purpose of describing embodiments of the invention and are not intended to limit the scope of the invention in any way. It will be apparent to those skilled in the art that various modifications and variations can be made in the cardiotomy reservoir and blood filter and their uses without departing from the spirit or scope of the invention. Thus, it is intended that the present invention cover the modifications and variations of this invention provided they come within the scope of the appended claims and their equivalents.

What is claimed is:

1. A blood filter comprising:
    a housing having a top portion, a base portion and a sidewall portion;
    a blood inlet;
    a filter element disposed within the housing and dividing the housing into an inlet chamber in flow communication with the blood inlet and an outlet chamber;
    the filter element comprising a portion of non-woven filter material and a portion of screen filter material, the non-woven filter material portion being in direct contact with the inlet chamber and in direct contact with the outlet chamber; and the screen filter material portion being in direct contact with the inlet chamber and in direct contact with the outlet chamber; and
    a blood outlet in flow communication with the outlet chamber.

2. The blood filter of claim 1, wherein the screen filter material portion contacts less of the inlet chamber than the non-woven filter material portion.

3. The blood filter of claim 1, wherein the blood inlet is located at the base portion of the housing and the blood outlet is located at the top portion of the housing.

4. The blood filter of claim 3, wherein the top portion of the housing has inclined surfaces converging upwardly towards the blood outlet.

5. The blood filter of claim 1, wherein the housing is generally rectangular.

6. The blood filter of claim 1, wherein the filter element is in the form of a continuous folded sheet.

7. The blood filter of claim 6, wherein the filter element is supported by a support and wherein the filter element has upper and lower ends which are embedded in potting.

8. The blood filter of claim 7, wherein the support for the filter element comprises a plurality of substantially parallel flaps that are H-shaped and are connected at a central region, so as to form a plurality of regions for blood passage.

9. The blood filter of claim 8, wherein the filter element comprises folds, each one of the folds of the portion of the filter element constituted by the non-woven filter material being supported by a half-flap of the support and the folds of the screen filter material portion of the filter element being disposed within two adjacent half-flaps of the support.

10. The blood filter of claim 1, wherein the inlet chamber is surrounded by the outlet chamber.

11. The blood filter of claim 1, wherein the non-woven filter material has a nominal porosity of from 10 to 100 microns.

12. The blood filter of claim 1, wherein the non-woven filter material has a nominal porosity of from 20 to 50 microns.

13. The blood filter of claim 1, wherein the non-woven filter material is a polyester felt.

14. The blood filter of claim 1, wherein the screen filter material has an aperture size of from 10 to 100 microns.

15. The blood filter of claim 1, wherein the screen filter material has an aperture size of from 20 to 50 microns.

16. The blood filter of claim 1, wherein the screen filter material is a polyester screen.

17. An extracorporeal circuit comprising a blood filter comprising:
    a housing having a top portion, a base portion and a sidewall portion;
    a blood inlet;
    a filter element disposed within the housing and dividing the housing into an inlet chamber in flow communication with the blood inlet and an outlet chamber;
    the filter element comprising a portion of non-woven filter material and a portion of screen filter material, the non-woven filter material portion being in direct contact with the inlet chamber and in direct contact with the outlet chamber; and the screen filter material portion being in direct contact with the inlet chamber and in direct contact with the outlet chamber, and
    a blood outlet in flow communication with the outlet chamber.

18. The extracorporeal circuit of claim 17, further comprising a blood reservoir in flow communication with the blood filter.

19. An extracorporeal circuit comprising a blood filter and a cardiotomy reservoir, wherein the blood filter is in flow communication with the cardiotomy reservoir, wherein the blood filter comprises:
    a first housing having a top portion, a base portion and a sidewall portion;
    a blood inlet;
    a filter element disposed within the first housing and dividing the first housing into an inlet chamber in flow communication with the blood inlet and an outlet chamber;
    the filter element comprising a portion of non-woven filter material and a portion of screen filter material, the non-woven filter material portion being in direct contact with the inlet chamber and in direct contact with the outlet chamber; and the screen filter material portion being in direct contact with the inlet chamber and in direct contact with the outlet chamber; and
    a blood outlet in flow communication with the outlet chamber; and
    wherein the cardiotomy reservoir comprises a second housing having a top portion, a bottom portion, and a continuous sidewall portion, the top portion and bottom portion connected to the sidewall portion to form an enclosed reservoir;
    the second housing having a blood inlet, a blood outlet, and an air outlet;
    the second housing having a trap at the bottom portion of the housing;
    the trap separating the second housing into the trap and a main portion of the second housing;
    the blood outlet being connected to a tube that allows blood to be drawn from the trap at the bottom portion of the second housing;
    the second housing having a filter interposed between the trap and the main portion of the second housing;
    and wherein the blood outlet is located on the top portion of the second housing.

* * * * *